United States Patent
Muehlradt

(10) Patent No.: US 7,435,790 B2
(45) Date of Patent: *Oct. 14, 2008

(54) DIHYDROXYPROPYL CYSTEINE PEPTIDE AND AGENT CONTAINING THIS PEPTIDE

(75) Inventor: Peter F. Muehlradt, Braunschweig (DE)

(73) Assignee: Helmholtz-Zentrum fuer Infektionsforschung GmbH, Braunschweig (DE)

(*) Notice: Subject to any disclaimer, the term of this patent is extended or adjusted under 35 U.S.C. 154(b) by 0 days.

This patent is subject to a terminal disclaimer.

(21) Appl. No.: 10/385,098

(22) Filed: Mar. 10, 2003

(65) Prior Publication Data

US 2003/0220265 A1 Nov. 27, 2003

Related U.S. Application Data

(62) Division of application No. 09/331,087, filed as application No. PCT/EP97/07090 on Dec. 17, 1997, now Pat. No. 6,573,242.

(30) Foreign Application Priority Data

Dec. 17, 1996 (DE) .............................. 196 52 586

(51) Int. Cl.
*A61K 38/04* (2006.01)
*A61K 39/00* (2006.01)
*C07K 7/08* (2006.01)

(52) U.S. Cl. .................... 530/327; 530/300; 514/14; 514/16; 514/669; 514/667; 514/772.3; 424/486; 424/180.1; 424/182.1

(58) Field of Classification Search ................ 514/14, 514/317, 18, 12; 530/326, 389, 359; 424/451, 424/400, 465, 1.85, 180.1, 182.1, 486
See application file for complete search history.

(56) References Cited

U.S. PATENT DOCUMENTS

| | | | | |
|---|---|---|---|---|
| 3,950,542 | A * | 4/1976 | Kalopissis et al. | 514/162 |
| 5,179,079 | A * | 1/1993 | Hansen et al. | 514/4 |
| 5,214,062 | A * | 5/1993 | Mark et al. | 514/369 |
| 5,358,933 | A * | 10/1994 | Porro | 514/15 |
| 5,788,962 | A * | 8/1998 | Wise et al. | 424/264.1 |
| 5,856,444 | A * | 1/1999 | Kawakita et al. | 530/350 |
| 6,376,203 | B1 * | 4/2002 | Matsuda et al. | 435/7.32 |
| 6,506,892 | B1 * | 1/2003 | Webb et al. | 536/23.7 |
| 6,573,242 | B1 * | 6/2003 | Muehlradt | 514/14 |
| 2002/0155117 | A1 * | 10/2002 | Suciu-Foca | 424/185.1 |
| 2004/0127405 | A1 * | 7/2004 | Muhlradt et al. | 514/12 |
| 2004/0249133 | A1 * | 12/2004 | Muhlradt et al. | 530/359 |
| 2005/0192217 | A1 * | 9/2005 | Muhlradt et al. | 514/12 |
| 2005/0276813 | A1 * | 12/2005 | Muhlradt et al. | 424/185.1 |
| 2006/0134061 | A1 * | 6/2006 | Muhlradt et al. | 424/78.27 |
| 2007/0203185 | A1 * | 8/2007 | Muhlradt et al. | 514/324 |

FOREIGN PATENT DOCUMENTS

| | | | |
|---|---|---|---|
| WO | 96/16987 | * | 6/1996 |
| WO | 98/27110 | * | 6/1998 |
| WO | 99/59610 | * | 11/1999 |

OTHER PUBLICATIONS

Swiss-Prot accession No. P94932, Monocytic differentiation/activation factor, name P48.*
Hall, Robert H et al, Biochem. J., vol. 319, pp. 919-927, 1996, cDNA and genomic cloning and expression of the P48 monocytic differentiation/activation factor, a *Mycoplasma fermentans* gene product.*
Muhlradt, Peter F. et al, J. Exp. Med. vol. 185, No. 22. Jun. 2, 1997, pp. 1951-1958, Isolation, structure elucidation and synthesis of a macrophage stimulatory lipopeptide from *Mycoplasma fermentans* acting at picomolar concentrations.*
Chambaud, I et al, Trends in Microbiology, vol. 7, No. 12, Dec. 1999, pp. 493-499, Interactions beween mycoplasma lipoproteins and the host immune system.*
Calcutt, M.J. et al, Infection and Immunity, Feb. 1999, vol. 67(2), pp. 760-771, Differential Posttranslational processing confers intraspecies variation of a major surface lipoprotein and a macrophage-activating lipopeptide of *Mycoplasma fermentans*.*
Galanos, C et al, Journal of Endotoxin Research, vol. 6(6), pp. 471-476, MALP-2, a Mycoplasma lipopeptide with classical endotoxic properties: end of an era of LPS monoply?.*
Wise, K.S. et al, Infection and Immunity, vol. 61(8), pp. 3327-3333, Aug. 1993, A Family of strain-variant lipoproteins of *Mycoplasma fermentans*.*
Bessler, WG et al, The Journal of Immunology, vol. 139(3), Sep. 1985, pp. 1900-1905.*
Kostyal, DA et al, Infection and Immunity, Sep. 1994, vol. 62(9), pp. 3793-3800.*
Muhlradt, PF et al, Infection and Immunity, vol. 59(11), pp. 3969-3974, Nov. 1991.*
Muhlradt, PF et al, Infection and Immunity, vol. 62(9), pp. 3801-3807, Sep. 1994.*
Muhlradt, PF e tal, Biochemistry, vol. 35, pp. 7781-7786, 1996.*
Quentmeier, H et al, Infection and Immunity, May 1990, vol. 58(5), pp. 1273-1280.*
Boslego, JW et al, Chapter 17, pp. 211-223, in Vaccines and Immunotherapy, 1991.*

(Continued)

*Primary Examiner*—Mark Navarro
*Assistant Examiner*—Ginny Portner
(74) *Attorney, Agent, or Firm*—Frommer Lawrence & Haug LLP; Ronald R. Santucci

(57) ABSTRACT

The invention relates to a S-(2,3-dihydroxypropyl)-cysteine peptide which has two long-chain fatty acids bonded in the form of esters at the dihydroxypropyl group, and which has the following sequence:

DhcGN NDE SNI SFK EK.

The invention relates also to a composition comprising the mentioned peptide.

1 Claim, No Drawings

OTHER PUBLICATIONS

Ellis, Ronald W, Chapter 29, New technologies for making vaccines, pp. 568-575, in Vaccines, WB Saunders Company, 1988.*
Hall et al (1996) reference of record.*
Matsumoto, M et al, J. Exp. Med., vol. 181, Jan. 1995, pp. 115-123.*
Matsumoto, M et al, The Journal of Biological Chemistry, vol 273(20), May 15, 1998, pp. 12407-12414, Structural and functional properties of Complement activating Protein M161Ag, a *Mycoplasma fermentans* Gene product that induces cytokine production by Human Monocytes.*
Jacobson, RM et al, Vaccine, vol. 19(2001), pp. 2438-2433, Adverse events and vaccination—the lack of power and predictability of infrequent events in pre-licensure study.*
Leece, JG et al, Can. J. Comp. Med., pp. 90-93, vol. 43, Jan. 1979.*
Lacombe, K et al, Vaccine, 2004, vol. 23, pp. 623-628.*
Graham, BS et al, JID, 2005, vol. 191, Mar. 1, 2005, pp. 647-649.*
Dazzi, F et al, Clinical Immunology and Immunopathology, vol. 75(1), Apr. 1995, pp. 26-32.*
Chambaud, Isabelle et al, Treands in Microbiology, vol. 7(12), 1999, pp. 493499.*
Uniprot Accession No. P94932, previously made for record.*
Hall, Robert E et al, Biochem. J, 1996, vol. 319, pp. 919-927, cDNA and genomic cloning and expression of the P48 monocytic differentiation/ activation factor, a *Mycoplasma fermentans* gene product.*
Morr, Michael et al, Eur. J. Immunol., 2002, vol. 32, pp. 3337-3347, Differential recognition of structural details of bacterial lipopeptides by toll-like receptors.*
Muhlradt, Peter F. et al, J. Exp. Med. vol. 185(11) Jun. 2, 1997.*
Muhlradt, Peter F et al, Biochemistry, 1996, vol. 35, pp. 7781-7786.*
Muhlradt, Peter F. et al, Infection and Immunity, Oct. 1998, vol. 66(10), pp. 4804-4810.*
Hall, Robert E. et al, Microbial Pathogenesis, 1999, vol. 27, pp. 145-153, Expression of the monocytic differentiation activation factor P48 in *Myoplasma* species.*
Hall, Robert E. et al, Biochemical and Biophysical REsearch Communications, vol. 269, pp. 284-289, 2000, Induction of Leukemia Cell Differnetiation and Apoptosis by Recombinant P48, a Modulin Derived from *Myocplasma fermentans*.*
Seya, Tsukasa et al, The International Journal of Biochemistry and Cell Biology, vol. 34, pp. 901-906, 2002, Molecules in Focus, A Lipoprotein family from *Myocplasm fermentans* confers host immune activation through Toll-like receptor 2.*
Rosati, Sergio et al, Infecion and Immunity, vol. 67(11), pp. 6213-6216, Nov. 1999, P48 Major Surface Antigen of *Mycoplasma agalactiae* is homologous to a malp product of *Myocplasma fermentans* and belongs to a Selected Family of Bacterial LIpoproteins.*
Hall et al (reference of record).*
Chambaud et al (reference of record).*

* cited by examiner

DIHYDROXYPROPYL CYSTEINE PEPTIDE AND AGENT CONTAINING THIS PEPTIDE

CROSS-REFERENCE TO RELATED APPLICATION

This application is a division of U.S. patent application Ser. No. 09/331,087 filed Jun. 16, 1999 now U.S. Pat. No. 6,573,242 entitled "Dihydroxypropyl-Cysteine Peptide and Agent Containing this Peptide" which is a 371 filing of international patent application PCT/EP97/07090 filed Dec. 17, 1997 which claims priority benefits of German Patent Application DE 1 96 52 586.1 filed Dec. 17, 1996.

The macrophage-stimulating activity of mycoplasma has been known for a relatively long time; see Loewenstein et al. in Cellular Immunology, 77 (1983) 290-297. It has also been assumed and formally proved that lipoproteins from mycoplasma exhibit such an activity; see Herbelin et al. in Infect. Immun., 62 (1994) 4690-4694 and Mühlradt et al. in Biochemistry, 35 (1996) 7781-7786. Lipoproteins from Gram-negative bacteria and analogues of those lipoproteins are likewise immunomodulators and have been described specifically as macrophage activators; see Melchers et al. in J. Exp. Med., 142 (1975) 473-482 and Hoffmann et al. in Immunobiol., 177 (1988) 158-170. Those species of lipoproteins carry an N-terminal S-(2,3-dihydroxypropyl)-cysteine group (Dhc) having three long-chain fatty acids, of which two are bonded in the form of esters and one is bonded in the form of an amide.

Lipoproteins and synthetic lipopeptide analogues have a half-maximum effective concentration (Max/2) of approximately $10^{-7}$ M; see Melchers et al. in J. Exp. Med., 142 (1975) 473-482 and Hoffmann et al. in Biol. Chem. Hoppe Seyler, 370 (1989) 575-582.

Synthetic analogues without the amide fatty acid have a half-maximum effective concentration (Max/2) of approximately $10^{-8}$M; see Metzger et al. in J. Peptide Scie., 3 (1995) 184-190. Furthermore, in Tertahedron, 45 (1989) 6331-6360, 6352, Baschang described a taurine-modified lipoprotein (sodium sulphonate; CGP-31362) which, according to Dong et al. in J. Exp. Med., 177 (1993) 1071-1077. still has macrophage-activating action as from 1 to 10 ng/ml of from 1 to $10 \times 10^9$ M. Finally, in J. Peptide Scie., 3 (1995) 184-190, Metzger et al. describes a Dhc peptide having the amino acid sequence CFE PPP ATT T (SEQ ID NO: 2), two palmitoyl groups being bonded to the 2,3-dihydroxypropyl group. The half-maximum effective concentration (Max/2) of that known peptide is 16 ng/ml or $10 \times 10^{-9}$ M.

There is, however, still a need for effective lipopeptides.

According to the invention there is now proposed a S-(2,3-dihydroxypropyl)-cysteine peptide having two fatty acids, which may be identical or different, bonded to the dihydroxypropyl group in the form of esters, the peptide having the following amino acid sequence (I):

```
DhcGN NDE SNI SFK EK (I) or 1                                                    13
Dhcys Gly Asn  Asn Asp Glu  Ser Asn Ile  Ser Phe Lys  Glu Lys
``` or an amino acid sequence that is identical to the sequence (I) except that the two N-terminal amino acids in positions 2 and, optionally, 3 are missing and/or one or two C-terminal amino acids have been deleted.

According to the invention, the two fatty acid radicals may have the formula R—CO—, wherein R is a $C_7$-$C_{25}$-alkyl, $C_7$-$C_{25}$-alkenyl or $C_7$-$C_{25}$-alkynyl radical, unsaturated radicals preferably being present in the cis configuration. Examples of $C_7$-$C_{25}$-alkyl, -alkenyl and -alkynyl radicals are $C_{16}$ and $C_{18}$ radicals.

According to the invention there is also provided a composition comprising a S-(2,3-dihydroxypropyl)-cysteine peptide according to the invention together with a conventional carrier and/or adjuvant. The composition according to the invention can be used for stimulating the synthesis of antibodies, for preventing infections (anti-infective activity), as an immunostimulant against tumours, for activating macrophages, for developing tolerance towards endotoxins or in the case of septic shock, especially in the case of Gram-negative bacteria, or as a vaccine adjuvant (admixture with a vaccine).

According to the invention, S-(2,3-dihydroxypropyl)-cysteine peptides can be prepared in a fully synthetic manner. The person skilled in the art can proceed analogously to the cited prior art. Reference is made also to DE 35 46 150 A1, DE 37 00 173 A1, DE 38 13 821 A1, DE 41 19 856 A1 and DE 43 29 309 A1.

The invention is explained in greater detail below with reference to an Example.

EXAMPLE

The lipopeptide is prepared from *Mycoplasma fermentans* (for example PG18). The isolation of the lipopeptide from mycoplasma is carried out by the following known separation procedure (Mühlradt et al. in Biochemistry, 35 (1996) 7781-7786).

(i) Delipidation of the mycoplasma using chloroform/methanol.
(ii) Extraction of the delipidated mycoplasma using hot 25 mM octyl glucoside.
(iii) Dialysis of the detergent extract.
(iv) Concentration of the extract by lyophilisation.
(v) Reversed-phase chromatography on a C8 column using a water/2-propanol gradient.

Detection of the biological activity is effected by measuring nitrite and nitrate as the secondary products of nitrogen monoxide, which is liberated on stimulation of interferon-treated murine peritoneal macrophages.

The active ingredient is a S-(2,3-dihydroxypropyl)-cysteine peptide which has two long-chain fatty acids (C16:0 and C18:0/C18:1) bonded in the form of esters at the dihydroxypropyl group, and which has the following sequence: Dhc-GNN DES NIS FKE K.

The most frequent molecular weight is 2164. In addition, it is possible to find variants which are distinguished by different fatty acids and by a peptide that is shortened by two C-terminal amino acids.

The substance has the property of stimulating macrophages of mice and humans to release cytokines and prostaglandins, with all the consequences of indirect stimulation of T and B lymphocytes; see Mühlradt et al. in Infect. Immun., 59 (1991) 3962-3968 and Feng & Lo in Infect. Immun., 62 (1994) 3916-3921. Its half-maximum effective concentration (Max/2) is 20 pg/ml or $10^{-11}$ M in the mouse system. That effective concentration is lower by a factor of from $10^2$ to $10^3$ than the corresponding known concentrations of similar natural or synthetic lipopeptides.

The invention claimed is:

1. An isolated S-(2,3-Dihydroxypropyl)-cysteine (Dhc) peptide having no more than two fatty acids, which fatty acids may be identical or different, bonded in the form of esters to the dihydroxypropyl group, the peptide having the following amino acid sequence (SEQ ID No. 1):

```
DhcGN NDE SNI SFK EK        (SEQ ID No. 1)
    2   5   10
``` with an exception selected from the following group:

(i) that the N-terminal amino acids in positions 2 (G=glycine) and, optionally 3 (N=aspargaine), are absent;

(ii) that the N-terminal amino acids in position 2 (G=glycine) and, optionally 3 (N=asparagine), are absent and one or two C-terminal amino acids are absent; or (iii) that one or two C-terminal amino acids are absent.

* * * * *

SEQUENCE LISTING

```
<160> NUMBER OF SEQ ID NOS: 2
<210> SEQ ID NO 1
<211> LENGTH: 14
<212> TYPE: PRT
<213> ORGANISM: Mycoplasma fermentans
<220> FEATURE:
<221> NAME/KEY: MOD_RES
<222> LOCATION: (1)..(1)
<223> OTHER INFORMATION: X is S-(2,3-dihydroxypropyl)-cysteine

<400> SEQUENCE: 1

Xaa Gly Asn Asn Asp Glu Ser Asn Ile Ser Phe Leu Glu Leu
1               5                   10

<210> SEQ ID NO 2
<211> LENGTH: 10
<212> TYPE: PRT
<213> ORGANISM: Rhodopseudomonas Viridis
<220> FEATURE:
<221> NAME/KEY: MOD_RES
<222> LOCATION: (1)..(1)
<223> OTHER INFORMATION: X is S-(2,3-dihydroxypropyl)-cysteine

<400> SEQUENCE: 2

Xaa Phe Glu Pro Pro Pro Ala Thr Thr Thr
1               5                   10
```